(12) United States Patent
Mitsuishi et al.

(10) Patent No.: US 7,878,992 B2
(45) Date of Patent: Feb. 1, 2011

(54) POWER ASSISTANCE CONTROLLING APPARATUS, POWER ASSISTANCE CONTROLLING METHOD, AND PHYSIOTHERAPY APPARATUS

(75) Inventors: Mamoru Mitsuishi, Tokyo (JP); Shinichi Warisawa, Tokyo (JP); Kazuo Yonenobu, Ashiya (JP); Nobuhiko Sugano, Suita (JP); Tatsuya Ishizuka, Soka (JP); Toji Nakazawa, Shinagawa (JP)

(73) Assignees: Mamoru Mitsuishi, Tokyo (JP); THK Co., Ltd., Tokyo (JP)

( * ) Notice: Subject to any disclaimer, the term of this patent is extended or adjusted under 35 U.S.C. 154(b) by 1063 days.

(21) Appl. No.: 10/557,543

(22) PCT Filed: May 21, 2004

(86) PCT No.: PCT/JP2004/006939
§ 371 (c)(1),
(2), (4) Date: Jan. 5, 2007

(87) PCT Pub. No.: WO2004/104719
PCT Pub. Date: Dec. 2, 2004

(65) Prior Publication Data
US 2007/0185418 A1 Aug. 9, 2007

(30) Foreign Application Priority Data
May 22, 2003 (JP) .............................. 2003-183560

(51) Int. Cl.
*A61H 1/02* (2006.01)
(52) U.S. Cl. .............................. 601/23; 601/27; 601/34
(58) Field of Classification Search ..................... 601/5, 601/23–26; 600/595
See application file for complete search history.

(56) References Cited

U.S. PATENT DOCUMENTS 5,056,038 A * 10/1991 Kuno et al. .................. 700/260

(Continued)

FOREIGN PATENT DOCUMENTS

EP 0 194 206 A1 9/1986

(Continued)

OTHER PUBLICATIONS

Japanese Office Action dated Dec. 1, 2009, issued in corresponding Japanese Patent Application No. 2003-183560.

(Continued)

*Primary Examiner*—Danton DeMille
(74) *Attorney, Agent, or Firm*—Westerman, Hattori, Daniels & Adrian, LLP

(57) ABSTRACT

Tow forces can be measured only by providing one force sensor in a device structure, and a drive system is driven so as to assist an external force by detecting it. A value at a force sensor (114) at the moment when a foot switch (121) is set as the original point (detection reference) of a force to be assisted. Variations of the force after the original point setting is measured by the force sensor (114) the difference between the measured value and the assist original point is obtained, and a force to be assisted is detected. Depending on the magnitude of the force to be assisted, assist operation is performed by causing a drive force to act on a foot such that the force to be assisted is reduced. When the force is assisted reaches zero, the assist operation is completed. Then, two forces, or "a force acting on a patient's foot" and "a force applied to the foot" from the outside, are detected by the one force sensor (114).

7 Claims, 10 Drawing Sheets

U.S. PATENT DOCUMENTS 5,255,188 A 10/1993 Telepko

FOREIGN PATENT DOCUMENTS

| EP | 1 364 636 A1 | 11/2003 |
| --- | --- | --- |
| JP | 5-310396 | 11/1993 |
| JP | 11-56888 | 3/1999 |
| JP | 11-198077 | 7/1999 |
| JP | 2001-270687 A | 10/2001 |
| JP | 2003-81598 | 3/2003 |
| JP | 2003-319958 | 11/2003 |
| WO | 02/092164 A2 | 11/2002 |
| WO | 03/105744 A2 | 12/2003 |

OTHER PUBLICATIONS

International Preliminary Report on Patentability dated Mar. 16, 2006 issued in corresponding PCT Application No. PCT/JP2004/006939.

European Search Report dated Jun. 5, 2009, issued in corresponding European Patent Application No. 04734348.8.

* cited by examiner

[FIG.1]
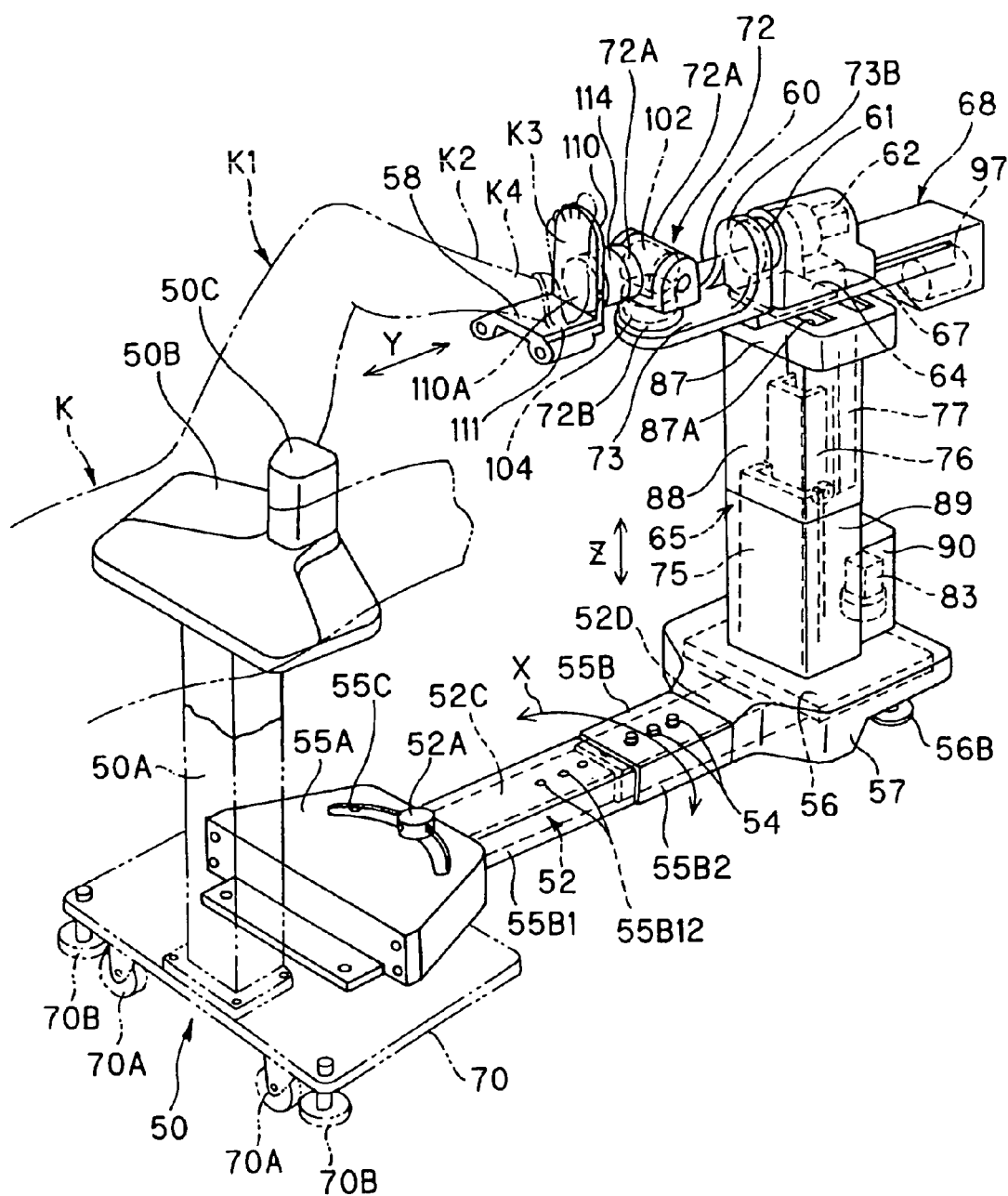

[FIG.2]
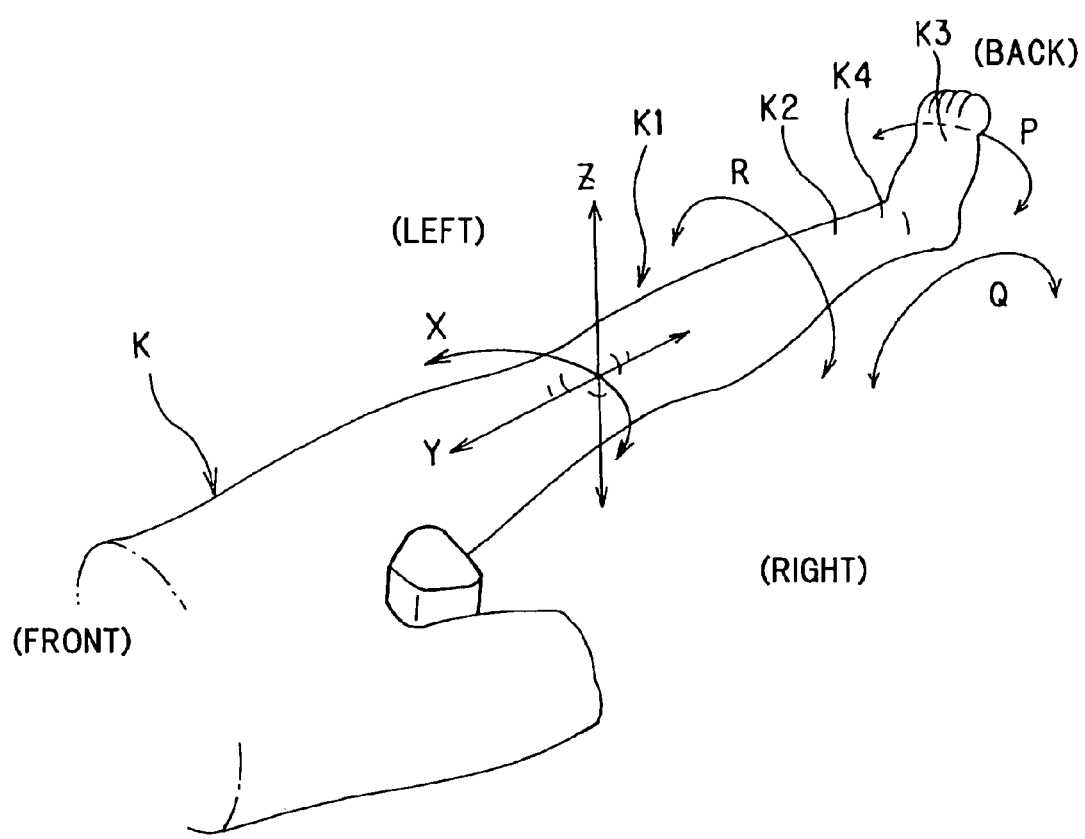

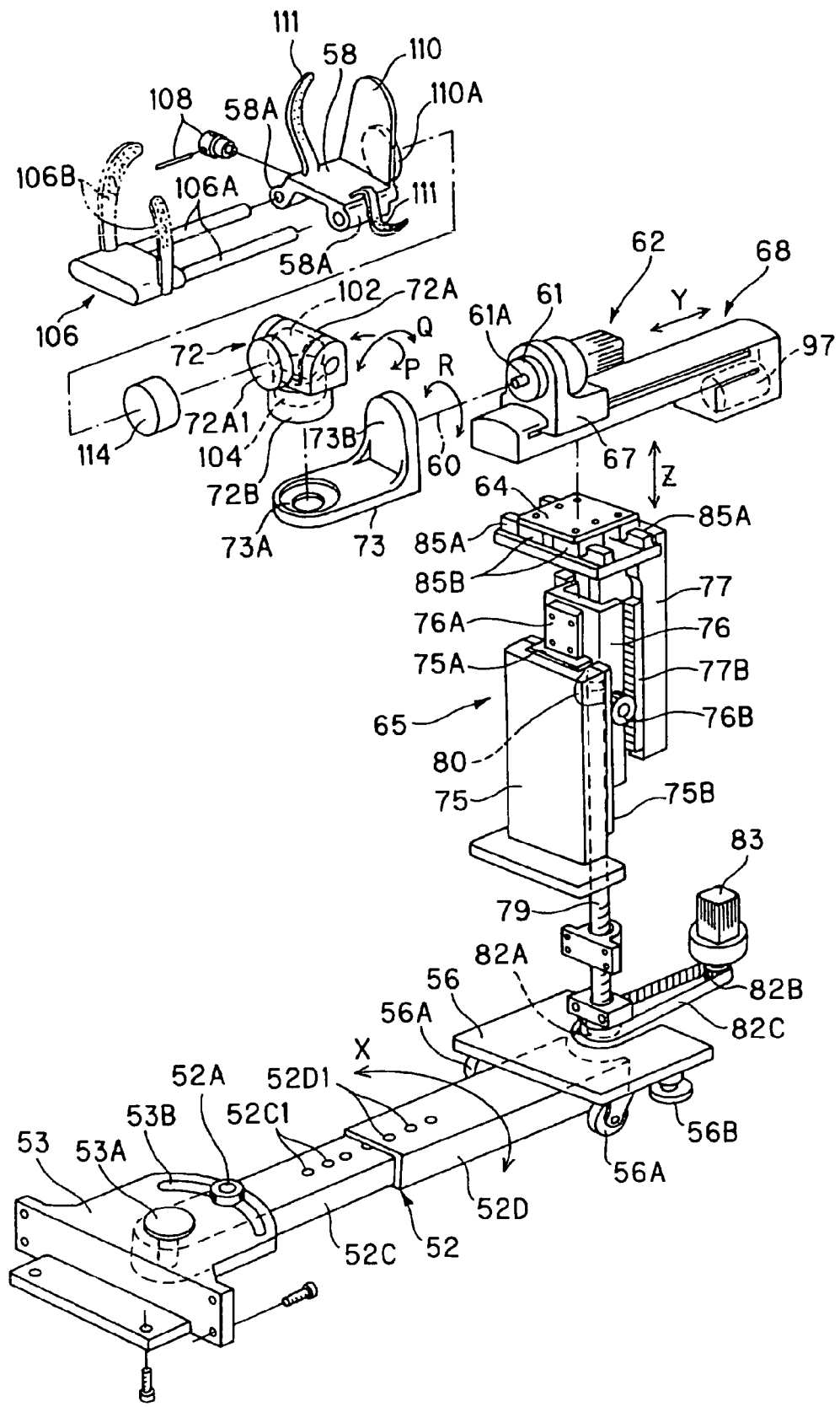
[FIG.3]

[FIG.4]
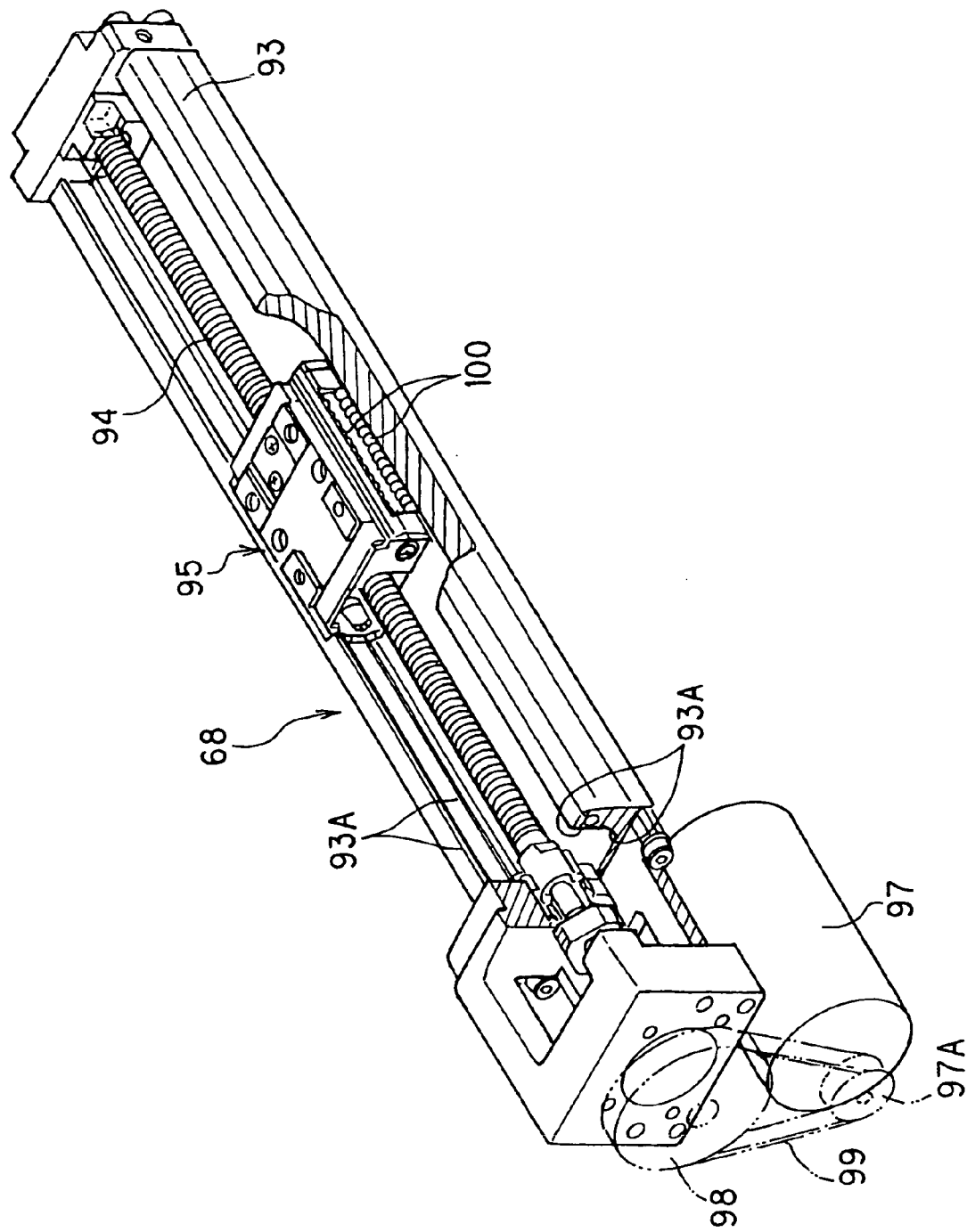

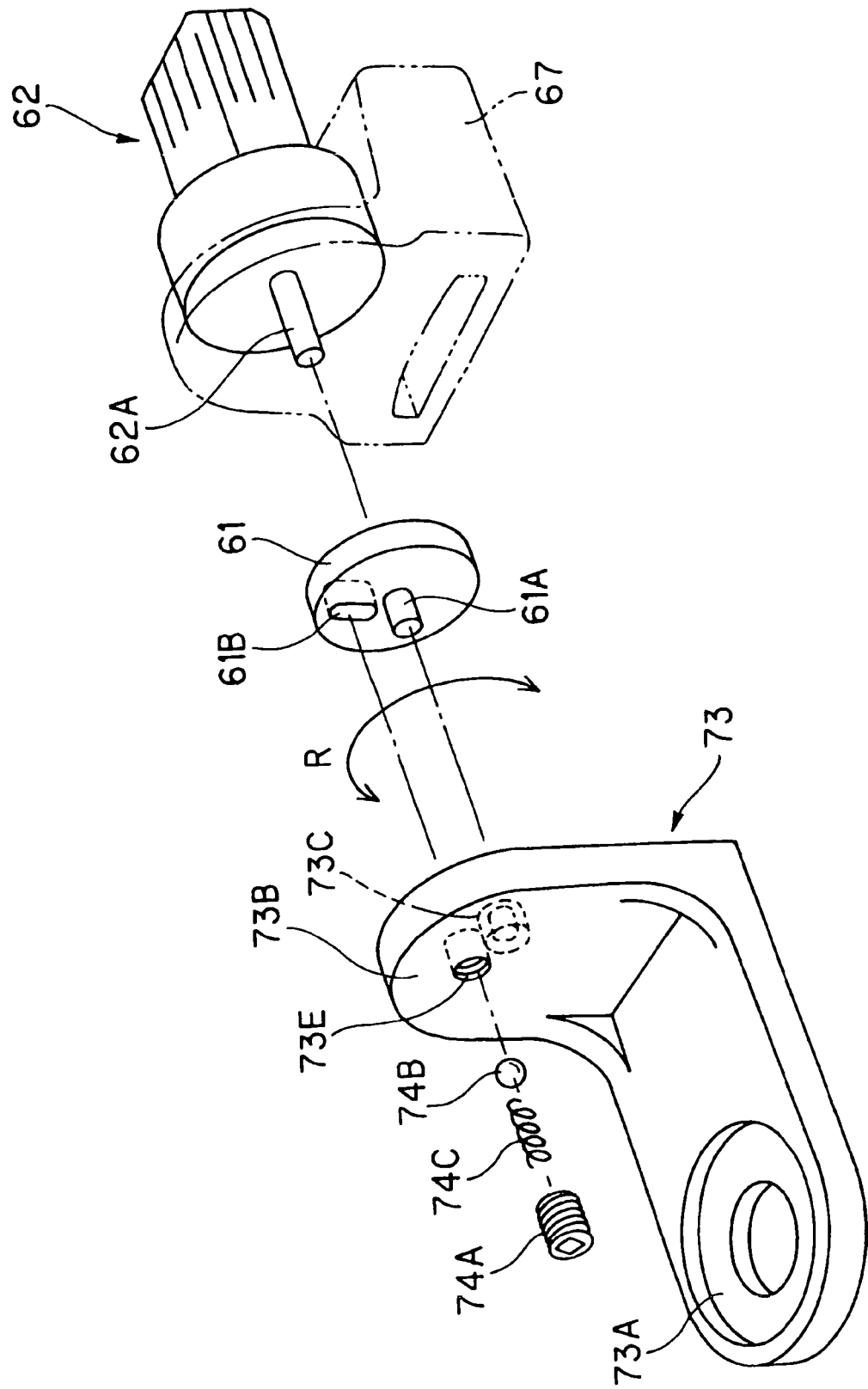
[FIG.5]

[FIG.6]
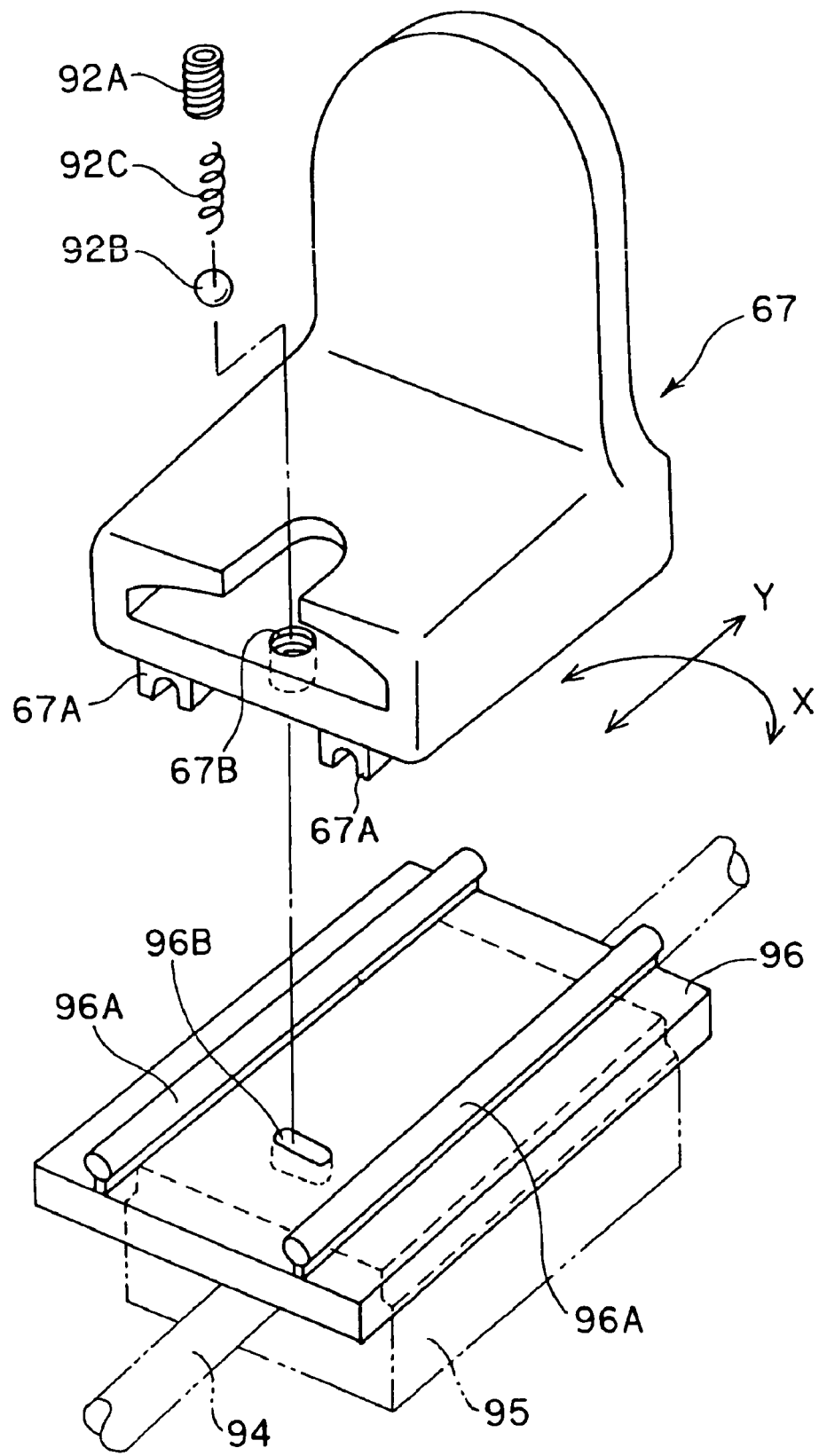

[FIG.7]
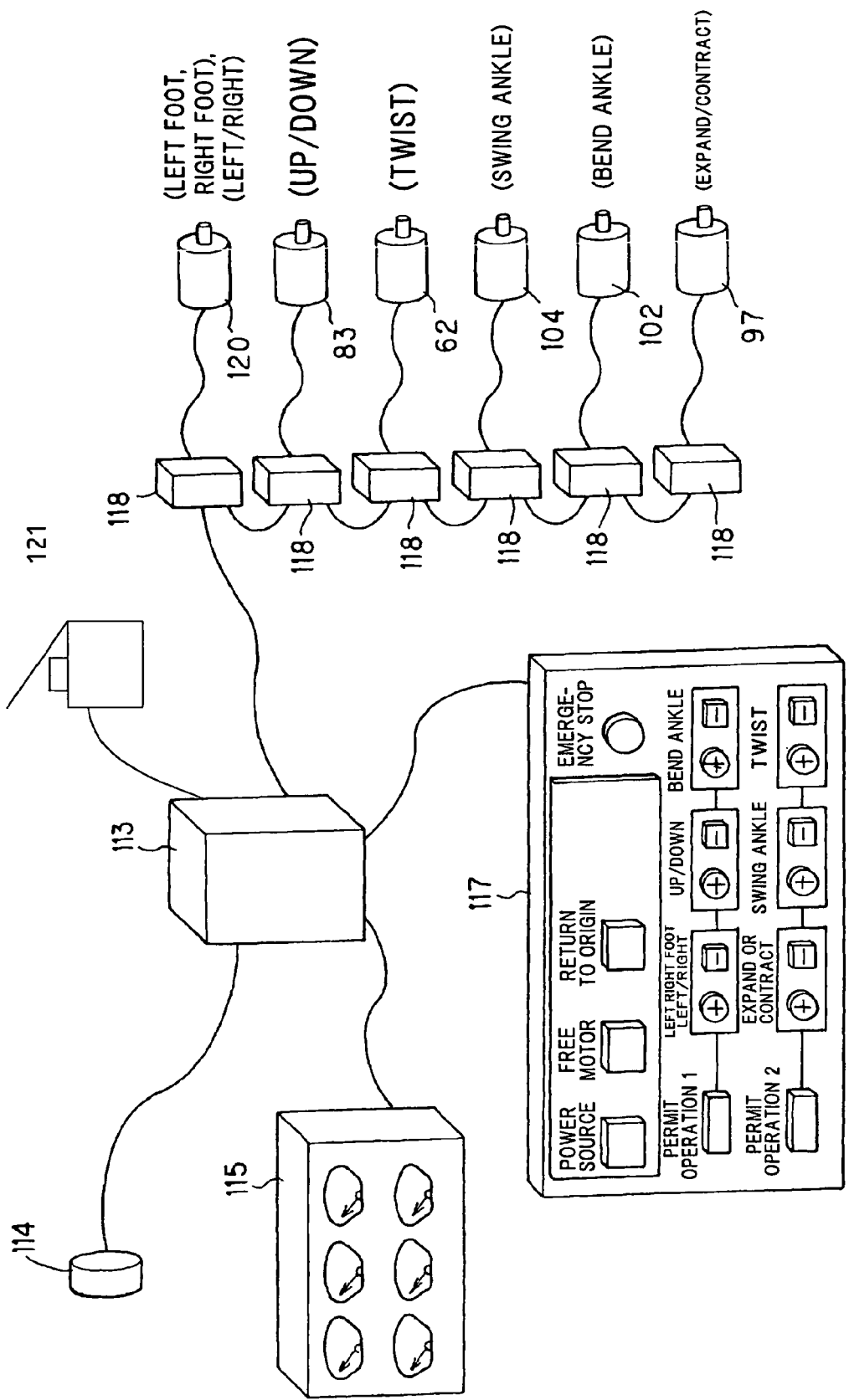

[FIG.8]
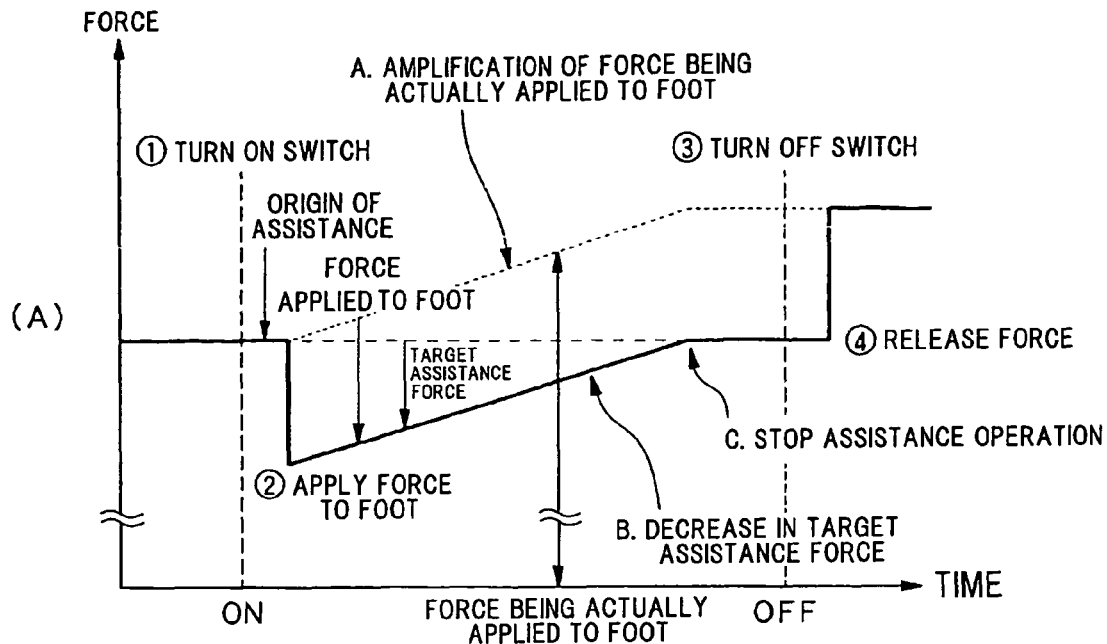
(A)
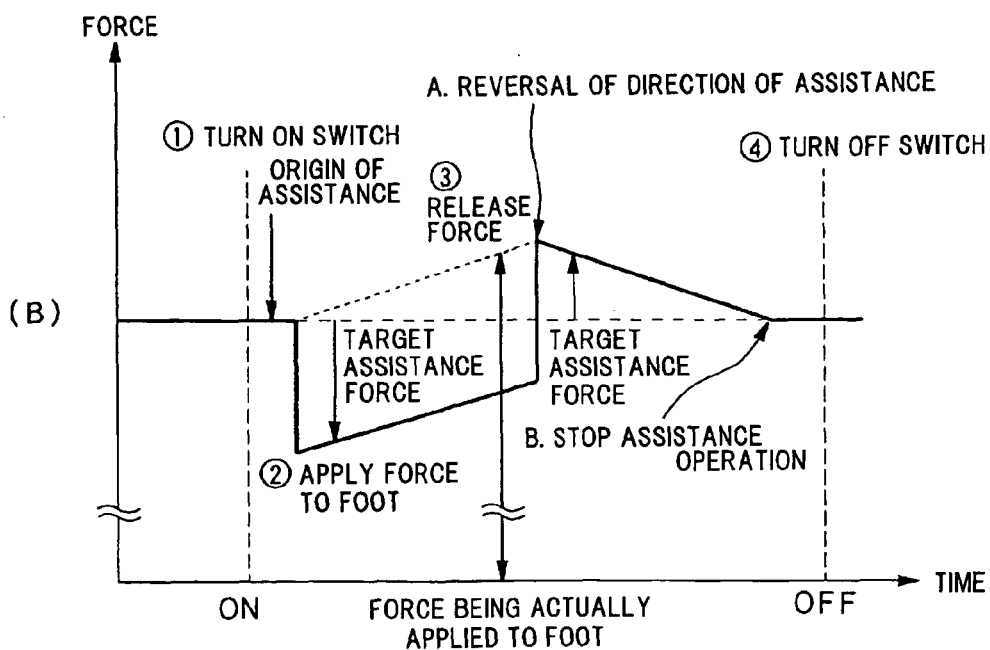
(B)

[FIG.9]
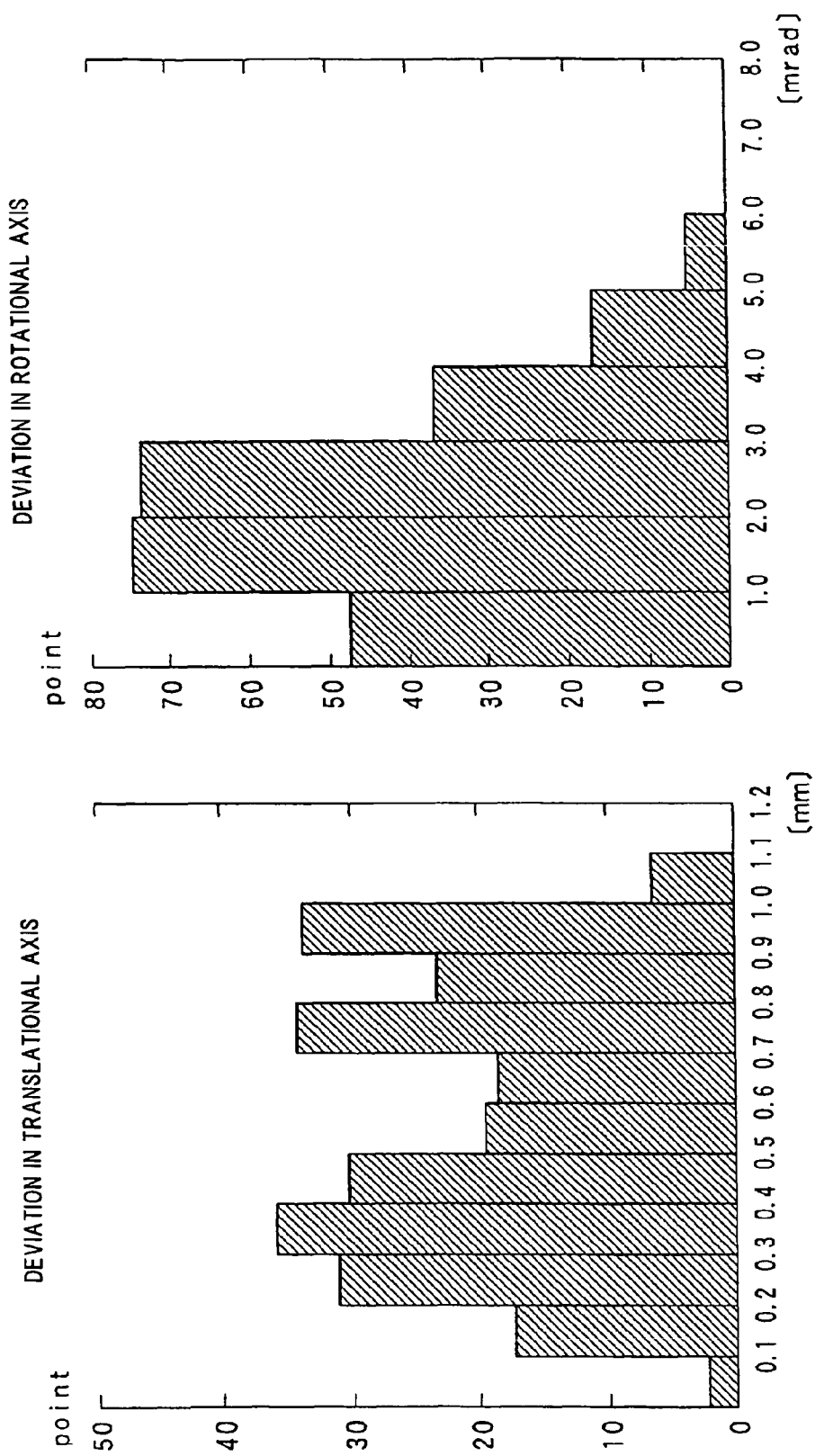

[FIG.10]
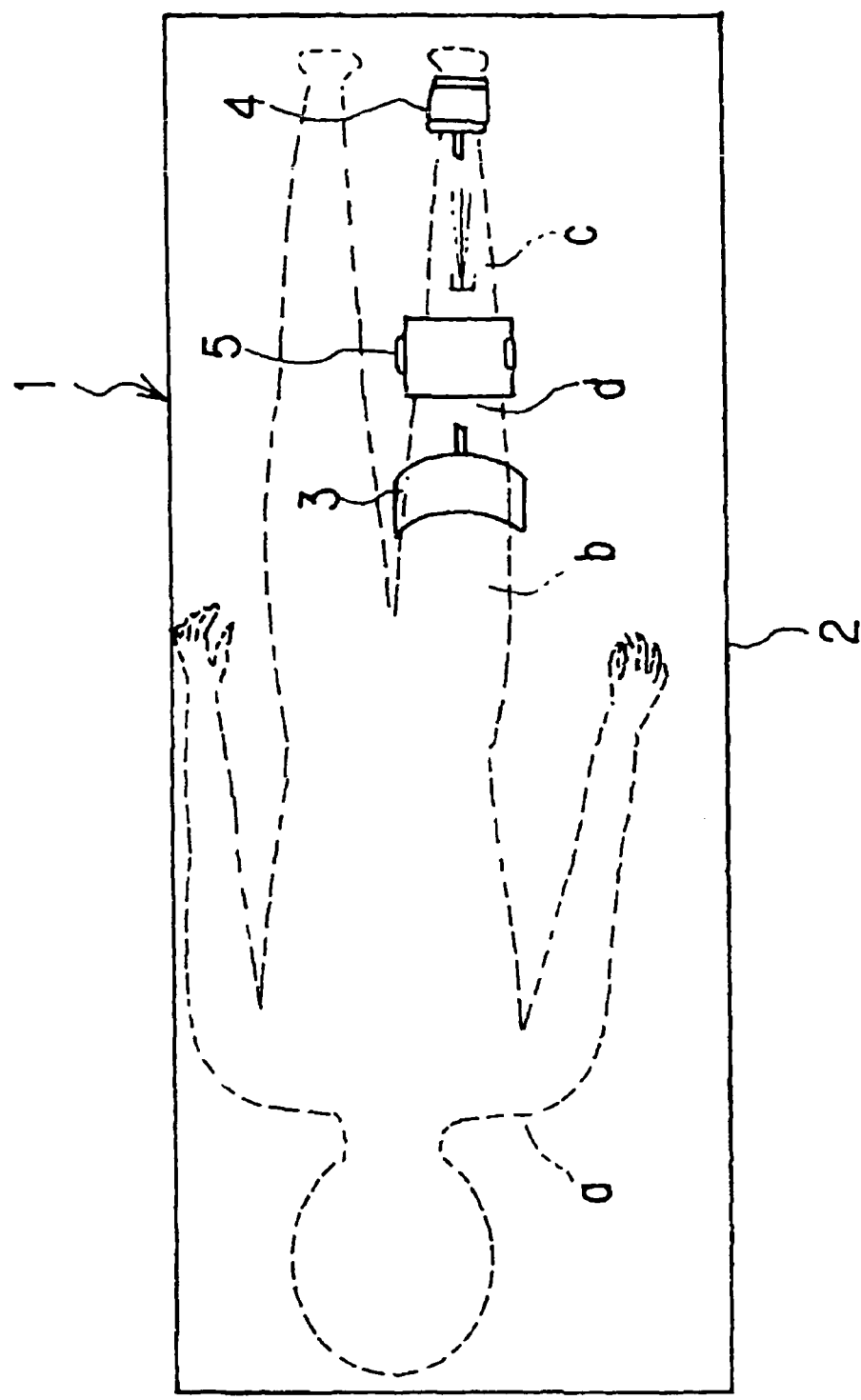

US 7,878,992 B2

POWER ASSISTANCE CONTROLLING APPARATUS, POWER ASSISTANCE CONTROLLING METHOD, AND PHYSIOTHERAPY APPARATUS

TECHNICAL FIELD

The present invention relates to a power assistance controlling apparatus, a power assistance controlling method, and a physiotherapy apparatus, and in particular, is suitably applicable to a physiotherapy apparatus used for giving a patient physiotherapy for a bone fracture in a femoral portion and the like.

BACKGROUND ART

When a person suffers a bone fracture or a dislocation, the person undergoes physiotherapy so as to treat the bone fracture or the dislocation. Conventionally, in the case of performing physiotherapy, a person performing physiotherapy such as a doctor or a physiotherapist causes the leg or the like of a patient perform various motions such as expanding, contracting, bending, and twisting by his own force.

However, a considerably large force is required to cause the leg or the like of a patient to perform various motions and hence the doctor or the physiotherapist forcibly suffers heavy work. Hence, patients that the doctor or the physiotherapist can give physiotherapy in a day are few in number.

Hence, an apparatus shown in FIG. 10 was proposed so as to solve such a problem. As shown in FIG. 10, this joint physiotherapy apparatus 1 includes a top board 2 on which a patient (a) lies on his back, femoral portion supporting means 3 for supporting a femoral portion (b) of the patient (a) in an up and slant manner, stretching means 4 for holding the ankle of the patient (a) and stretching the lower leg (c) in a long axial direction, and rolling means 5 for holding a tibia head portion (d) and rolling it in a vertical direction with respect to the long axis of the lower leg (c) (refer to patent document 1).

In this joint physiotherapy apparatus 1, the knee of the patient (a) can be expanded and contracted by operating the stretching means 4 and at the same time the knee can be swung to the left and right by operating the rolling means 5.

[Patent document 1] Japanese Unexamined Patent Publication No. 11-56888

DISCLOSURE OF THE INVENTION

Problems that the Invention is to Solve

However, the conventional joint physiotherapy apparatus 1 can cause the knee of the patient (a) only to expand and contract and to swing to the left and right and hence can not be used for performing physiotherapy.

That is, at the time of performing physiotherapy, not only the operation of causing the leg of the patient to expand and contract but also, in particular, the operation of causing the lower leg to twist is frequently performed. Moreover, in many cases, other operations, that is, the operation of causing the lower leg to move up and down and to the left and right and the operations of causing an ankle to perform various motions are also required. The doctor or the physiotherapist has to perform these operations by the use of his force with the help of several assistants.

Hence, developments are being made in a physiotherapy apparatus capable of performing all operations of physiotherapy, which are now performed by the doctor, the physiotherapist and the like, by the use of their forces, by the use of a machine.

However, in the case of giving a patient physiotherapy by the use of a physiotherapy apparatus, an operation is performed on the ankle of the patient. For this reason, in some cases, all force applied to the ankle is not applied to the whole lower leg to the base of leg of the patient and a delicate adjustment is required. Under these circumstances, there has been desired a method for performing the operations while the doctor, the physiotherapist, and the like is actually touching the lower leg of the patient when they give the patient physiotherapy.

However, when the doctor, the physiotherapist, and the like give the patient physiotherapy, in the case of applying a force to the leg of the patient, they have to apply as large a force as approximately 294 N (30 kgf). At this time, as described above, the forces of a plurality of persons such as the doctor, the physiotherapist, and assistant are required.

Hence, the present inventor has developed a technology for assisting the action of forces by the doctor and the physiotherapist in a physiotherapy apparatus, that is, a technology for a so-called power assistance control. However, at least two force sensors are required to perform a power assistance control.

That is, in the case of employing a physiotherapy apparatus having a power assistance controlling function in performing physiotherapy, it is necessary to measure a force existing in performing physiotherapy. As this force are thought to be "a force applied to the leg of the patient", which is applied by the physiotherapy apparatus, and "a force applied to a member (boot) for holding the leg of the patient", which is applied from outside by the doctor, the physiotherapist, and the like.

Then, according to the findings of the present inventor, to measure these two forces respectively, these two forces need to be measured by two force sensors, respectively. However, these force sensors are extremely expensive and hence it is desirable to reduce the number of force sensors used for the apparatus to a minimum necessary number. Then, it has been eagerly desired to develop a technology capable of measuring the above-mentioned two forces by one force sensor.

Therefore, the object of this invention is to provide a power assistance controlling apparatus and a power assistance controlling method, which can compute two forces by providing an apparatus with only one force sensor in the construction and can drive a driving system in such a way as to assist a force applied from outside.

Moreover, other object of this invention is to provide a physiotherapy apparatus that can perform an operation required to give a patient physiotherapy for his lower leg and can perform a power assistance control capable of assisting a physiotherapy operation by a physiotherapist and facilitating the physiotherapy operation by a physiotherapist while keeping safety.

Means for Solving the Problems

To achieve above-mentioned object, according to a first aspect of the present invention, there is provided a power assistance controlling apparatus comprising:

force detecting means constructed so as to detect a force applied to an object and having one detection point;

driving means for applying a force to the object;

switching means for controlling turning on/off the driving means; and control means for controlling the driving means and constructed so as to communicate, data with the force detecting means, wherein a force effected by applying a force to the object from outside is measured by the force detecting means with reference to a detection reference of a force measured by the force detecting means at timing when the driving means is turned on by the switching means, and wherein an assistance force can be applied to the object by the driving means in such a way as to decrease a difference between the measured force and the detection reference.

According to a second aspect of the present invention, there is provided a power assistance controlling method characterized in: that a force applied to an object is detected by a force detecting means having one detection point; that when a force is applied to the object from outside, a force effected by applying the force to the object from outside is measured by the force detecting means with reference to a detection reference of a force measured by the force detecting means when driving means is turned on by switching means for controlling turning on/off the driving means by control means constructed so as to communicate data with the force detecting means; and that an assistance force is applied to the object by the driving means in such a way as to decrease a difference between the measured force and the detection reference.

According to a second aspect of the present invention, there is provided a physiotherapy apparatus comprising:

a power assistance controlling mechanism that includes: force detecting means constructed so as to detect a force applied to an object and having one detection point; driving means for applying a force to the object; switching means for controlling turning on/off the driving means; and control means for controlling the driving means and constructed so as to communicate data with the force detecting means, and is constructed in such a way that a force effected by applying a force to the object from outside is measured by the force detecting means with reference to a detection reference of a force measured by the force detecting means when the driving means is turned on by the switching means, and that an assistance force can be applied to the object by the driving means in such a way as to decrease a difference between the measured force and the detection reference.

In this invention, preferably, a force applied to an object by driving means is applied until a difference between a force measured as a result effected by applying a force to the object from outside by force detecting means (force measuring means) and a detection reference (measurement reference) comes nearly to zero.

In this invention, typically, the force detecting means is a six-axial force sensor capable of detecting translational three axial directions and rotational three axial directions.

The technical principle of this invention is not necessarily limited to the above-mentioned combination but includes technical principles realized by combining the above-mentioned inventions arbitrarily as appropriate.

Effect of the Invention

As described above, according to a power assistance controlling apparatus and a power assistance controlling method in accordance with this invention, it is possible to measure two forces only by providing the apparatus with one force sensor in the construction and to detect a force applied from outside and to drive a driving system in such a way as to assist in amplifying the force applied from outside.

Moreover, according to a physiotherapy apparatus in accordance with this invention, it is possible to perform operations necessary for reducing the lower leg of a patient and to assist a physiotherapy operation by a physiotherapist and to facilitate the physiotherapy operation by the physiotherapist while keeping safety. As a result, even if a physiotherapist is powerless, the physiotherapist can give a patient sufficient physiotherapy while keeping safety.

BRIEF DESCRIPTION OF THE DRAWINGS

FIG. 1 is a perspective view showing a physiotherapy unit of a physiotherapy apparatus according to one embodiment of this invention.

FIG. 2 is a diagram showing operations that the physiotherapy unit of a physiotherapy apparatus according to one embodiment of this invention can cause the lower leg of a patient to perform.

FIG. 3 is an exploded view in perspective of the physiotherapy unit of a physiotherapy apparatus according to one embodiment of this invention.

FIG. 4 is a perspective view, partly in cross section, showing third driving means mounted in the physiotherapy apparatus according to one embodiment of this invention.

FIG. 5 is an exploded view in perspective showing a mechanical safety switch in a direction to twist a lower leg, which is mounted in the physiotherapy apparatus according to one embodiment of this invention.

FIG. 6 is an exploded view in perspective showing a mechanical safety switch in a direction to expand and contract a lower leg, which is mounted in the physiotherapy apparatus according to one embodiment of this invention.

FIG. 7 is a diagram showing a control section mounted in the physiotherapy apparatus according to one embodiment of this invention.

FIGS. 8A and 8B are graphs showing power assistance control according to one embodiment of this invention.

FIGS. 9A and 9B are graphs showing a result of verification test on trajectory accuracy when a spline interpolation driving control in the physiotherapy apparatus according to one embodiment of this invention is performed.

FIG. 10 is a diagram showing a joint physiotherapy apparatus according to related art.

BEST MODE FOR CARRYING OUT THE INVENTION

Hereinafter, an embodiment of this invention will be described with reference to the drawings. Then, like or corresponding parts are designated by like reference numerals throughout the drawings of the following embodiment.

First, a physiotherapy apparatus according to one embodiment of this invention will be described.

In FIG. 1 is shown a physiotherapy unit according to this one embodiment. The physiotherapy apparatus according to this one embodiment is constructed of a physiotherapy unit referred to as a so-called physiotherapy robot and a control section for controlling this physiotherapy unit.

(Physiotherapy Unit)

As shown in FIG. 1, the physiotherapy unit according to this one embodiment is used for giving a patient K physiotherapy on his lower leg K1 and is provided with a support base 50 for supporting at least the lower half of the body of the patient K whose lower leg K1 needs to be reduced. The patient K is shown also in FIG. 2.

A swing arm 52 formed in a linear shape is mounted on the support base 50 in such a way as to swing freely in a nearly horizontal plane. Specifically, a mounting plate 53 shown in FIG. 3 is mounted on the support base 50 by a bolt and the swing arm 52 is mounted at the base end of this mounting plate 53 by a support pin 53A in such a way as to swing freely.

Moreover, a positioning bolt 52A is screwed in a portion near the base end of the swing arm 52 and the neck of the bolt 52A is inserted into an arc-shaped guide groove 53B formed in the mounting plate 53. That is, the swing arm 52 is swung to a desired position in a state where this positioning bolt 52A is loosened and after the positioning of the swing arm 52 is finished, the positioning bolt 52A is again screwed in.

The driving, that is, swinging of the swing arm 52 is performed by a manual operation by a doctor or a physiotherapist or arm driving means (not shown, but only a motor included as a driving source is shown by a reference numeral 120 in FIG. 7). In the case of automatically performing the operation of swinging the swing arm 52 by this arm driving means, it is preferable to automatically perform the operation of positioning of the swing arm 52 and the operation of releasing the positioned swing arm 53 by replacing the above-mentioned positioning bolt 52A with an electromagnetic chuck (not shown) or the like.

As shown in FIG. 1, there are provided covers 55A, 55B for covering the mounting plate 53 and the swing arm 52, and an arc-shaped opening 55C for avoiding interference with the positioning bolt 52A is formed in this cover 55A.

As shown in FIG. 1 and FIG. 3, a support plate 56 is fixed to the free end of the swing arm 52. This support plate 56 is provided with casters 56A for easily swinging the swing arm 52 on a floor and a stopper 56B for stopping and fixing the swing arm 52 at an arbitrary position. The support plate 56 is also covered with a cover 57 shown in FIG. 1.

In the case of automatically performing the operation of swinging the swing arm 52 by the arm driving means, the positioning bolt 52A is replaced with the electromagnetic chuck (not shown) or the like and at the same time the stopper 56B is replaced with a member capable of automatically fixing the swing arm 52 and releasing the fixed swing arm 52.

A lower thigh supporting base 58 for supporting the lower thigh K2 of the patient K is arranged directly above the swing arm 52. The swing arm 52 is used for swinging this lower thigh supporting base 58 in an early horizontal plane.

As shown in FIG. 1 and FIG. 3, the physiotherapy unit 5 is provided with a first movable table 61 for moving, that is, rotating the lower thigh supporting base 58 around a nearly horizontal axis 60 and a motor 62 as first driving means to rotate and drive this first movable table 61.

Moreover, the physiotherapy unit 5 is provided with a third movable table 64 for moving the lower thigh supporting base 58 in a nearly vertical direction, third driving means 65 for driving this third movable table 64, a second movable table 67 for moving the lower thigh supporting base 58 in a nearly horizontal direction, and second driving means 68 for driving this second movable table 67.

The above-mentioned swing arm 52, the first movable table 61, the second movable table 67, the third movable table 64, and the lower thigh supporting base 58 are mounted on the support base 50 stepwise in a specified order. In this one embodiment, the swing arm 52, the third movable table 64, the second movable table 67, the first movable table 61, and the lower thigh supporting base 58 are mounted stepwise in this order and the first movable table 61 of the final step is mounted with the lower thigh supporting base 58.

In this regard, the order of mounting the swing arm 52 and the respective movable tables 61, 67, 64 is not limited to the order in this embodiment but can be changed as appropriate.

The above-mentioned swing arm 52 is used for moving the lower leg K1 of the patient K shown in FIG. 1 and FIG. 2 to the left and right (in a direction shown by arrow X), that is, for swinging the lower leg K1, and for positioning the lower thigh supporting base 58 in correspondence with any one of the left and right legs of the patient K.

Moreover, the first movable table 61 is used for twisting the lower leg K1 of the patient K (in a direction shown by arrow R), and the second movable table 67 is used for moving the lower leg K1 back and forth (in a direction shown by arrow Y), that is, for expanding and contracting the lower leg K1, and the third movable table 64 is used for moving the lower leg K1 up and down (in a direction shown by arrow Z).

Next, the respective above-mentioned constituent elements will be described. First, the support base 50 for supporting at least the lower half of the body of the patient K will be described.

That is, as shown in FIG. 1, the support base 50 is provided with a base 70 of the base part of the apparatus, a leg part 50A whose bottom end is fixed to this base 70, and a place part 50B mounted on the top end of the leg part 50A and having the buttocks of the patient K placed thereon. This place part 50B is provided with a column 50C to be put on the crotch of the patient K in order to prevent the patient K from moving while the patient K undergoes physiotherapy.

The base 70 is provided with casters 70A for carrying the physiotherapy apparatus and stoppers 70B for stopping and fixing the apparatus carried to an arbitrary position.

Successively, the first movable table 61 and the motor (first driving means) 62 for moving the lower thigh supporting base 58 around a nearly horizontal axis 60, that is, for twisting the lower leg K1 of the patient (in a direction shown by arrow R) and the construction around them will be described.

As shown in FIG. 1 and FIG. 3, the first movable table 61 is formed in the shape of a disk and is mounted on the output shaft (which will be described later) of the motor 62. The lower thigh supporting base 58 is coupled to this first movable table 61 via a universal coupling 72 and an intermediary plate 73 in succession.

The universal coupling 72 interposed between the lower thigh supporting base 58 and the first movable table 61 is provided with a coupling member 72A that can move freely, that is, rotatable around a nearly horizontal axis, and a second coupling member 72B that constructs the universal coupling 72 with this first coupling member 72A and can move freely, that is, rotatable around a nearly vertical axis.

A circular seat 73A is formed at the front end of the intermediary plate 73 and the bottom end of the second coupling member 72B is fitted in this seat 73A. Moreover, the rear end 73B of the intermediary plate 73 is fitted on the first movable table 61.

Next, the third movable table 64, the third driving means 65, and their peripheral construction, which move the lower thigh supporting base 58 in the nearly vertical direction, that is, move the lower leg K1 of the patient up and down (in the direction shown by arrow Z), will be described.

As shown in FIG. 1, a guide member 75 is erected on the support plate 56 mounted on the free end of the swing arm 52. The third movable table 64 is mounted on this guide member 75 in such a way as to move freely up and down (in the direction shown by arrow Z).

Specifically, as shown in FIG. 3, an intermediate member 76 is mounted on the guide member 75 in such a way as to move freely up and down and a lifting and lowering member 77 is mounded on this intermediate member 76 in such a way as to move freely up and down. The third movable table 64 is mounted on the top end of this lifting and lowering member 77.

More specifically, a track rail 76A is fixed to one side of the intermediate member 76 and is guided by a block 75A fixed to the side of the guide member 75, whereby the intermediate member 76 is guided up and down.

Although not shown, the same track rail and the block are provided also to the other side of the intermediate member 76 and the side of the lifting and lowering member 77 opposed to the side, whereby the lifting and lowering member 77 is guided up and down.

As shown in FIG. 3, racks 75B, 77B are provided on the surfaces opposed to each other of the guide member 75 and the lifting and lowering member 77, respectively. Then, a pinion 76B provided on the intermediate member 76 is engaged with these racks 75B, 77B. With this, a so-called double-speed mechanism is constructed.

A ball screw shaft 79 is erected on and rotatably supported by the support plate 56. Meanwhile, the intermediate member 76 has a ball screw nut 80 built in and the ball screw shaft 79 is screwed in the ball screw nut 80. A large-diameter toothed belt wheel 82A is fitted on the bottom end of the ball screw shaft 79.

A motor 83 is arranged near this toothed belt wheel 82A and a small-diameter toothed belt wheel 82B is fitted on the output shaft of the motor 83. Then, a toothed belt 82C is looped around both toothed belt wheels 82A and 82B.

The third driving means 65 is constructed in the above-mentioned manner. In the construction like this, when the motor 83 is operated, the ball screw shaft 79 is rotated and driven to move up or down the ball screw nut 80 screwed on the ball screw shaft 79, whereby the intermediate member 76 combined integrally with the ball screw nut 80 is moved up or down.

Then, the pinion 76B provided on the intermediate member 76 rolls along the rack 75B of the guide member 75 in the state of engagement and hence the lifting and lowering member 77 having the rack 77B engaged with the pinion 76B moves up or down. Hence, the third movable table 64 moves up or down to move the lower thigh supporting base 58.

In this regard, the third movable table 64, hence, the lower thigh supporting base 58 can move in the left and right direction (in the direction shown by arrow X) with respect to the lifting and lowering member 77. That is, as shown in FIG. 3, track rails 85A are mounted on the top end of the lifting and lowering member 77 in a manner extending in the left and right direction. Then, a moving block 85B is fixed to the bottom surface of the third movable table 64 and is engaged with the track rails 85A in such a way as to be able to move freely.

In this regard, as shown in FIG. 1, there are provided covers 87 to 90 for covering the above-mentioned third movable table 64 and second driving means 65. Here, an opening 87A through which the moving block 85B can reciprocate is formed in the cover 87 for covering the third movable table 64. Moreover, the cover 88 for mainly covering the lifting and lowering member 77 can move in the up and down direction with respect to the cover 89 for mainly covering the fixed side guide member 75.

Successively, the second movable table 67 and the second driving means 68, which move the lower thigh supporting base 58 in the nearly horizontal direction, that is, move the lower leg K1 of the patient back and force (in the direction shown by arrow Y), in other words, expand and contract the lower leg K1, and their peripheral construction will be described.

This second driving means 68 is constructed of a linear driving unit shown in FIG. 4. FIG. 4 shows the internal structure of the second driving means 68 with its cover removed. As shown in the drawing, this second driving means 68 is provided with an outer rail 93 having high rigidity and shaped like a letter U in cross section, a ball screw shaft 94 arranged in the hollow portion of the outer rail 93 and rotatably mounted on both ends of the outer rail 93 via bearings, and an inner block 95 including a ball screw nut (not shown) screwed on the ball screw shaft 94. The second movable table 67 is secured to the top surface of the inner block 95 by bolts.

A motor 97 is mounted at one end of the outer rail 93 (shown in FIG. 1 and FIG. 3). A small-diameter toothed belt wheel 97A is fitted on the output shaft of the motor 97. Then, a large-diameter toothed belt wheel 98 is coupled to one end of the ball screw shaft 94 via a coupler or the like. A toothed belt 99 is looped around both toothed belt wheels 97A and 98.

The outer rail 93 has, for example, two ball rolling grooves 93A formed on each side of its inner surface along the whole length. The inner block 95 is provided with endless circulation passages each including a load ball rolling groove corresponding to these ball rolling grooves 93A and many balls 100 are arranged and received in the respective endless circulation passages.

The second driving means 68 is constructed in the manner described above. In the construction like this, when the motor 97 is operated, the ball screw shaft 94 is rotated and driven to move the inner block 95 including the ball screw nut screwed on the ball screw shaft 94, whereby the third movable table 67 secured to the inner block 95 is moved. Then, the lower thigh supporting base 58 is moved in the nearly horizontal direction.

While the physiotherapy apparatus has the above-mentioned construction as a main construction, the physiotherapy apparatus has a construction to be described later added thereto.

That is, in the coupling member 72A (freely moving, that is, rotating around a nearly horizontal axis) included by the universal coupling 72 shown in FIG. 1 and FIG. 3 is built a hollow motor 102 as fourth driving means for rotating the coupling member 72A around its rotational central axis. Then, in the second coupling member 72B (freely moving, that is, rotating around a nearly vertical axis) constructing the universal coupling 72 along with the coupling member 72A is built a hollow motor 104 as fifth driving means for rotating the second coupling member 72B around its rotational central axis.

In the construction like this, when the hollow motor 102 is operated, the lower thigh supporting base 58 is moved in the direction shown by arrow Q. That is, it is possible to bend the ankle K4 of the patient back and forth. Then, when another hollow motor 104 is operated, the lower thigh supporting base 58 is moved in the direction shown by arrow P. With this, it is possible to swing the ankle K4 of the patient to the left and right.

By the way, as is clear from FIG. 1 and FIG. 3, the lower thigh supporting base 58 is formed in the shape of a table of an appropriate size so as to hold the foot K3 and lower thigh K2 of the patient K with their lower sides placed thereon.

Moreover, as shown in FIG. 3, the lower thigh supporting base 58 is mounted, as required, with an auxiliary table 106, that is, an auxiliary member that can be expanded and contracted in the longitudinal direction of the lower thigh K2 and can be freely mounted and dismounted. The auxiliary table 106 is provided with a pair of rods 106A and the pair of rods 106A can be inserted into sleeves 58A formed in the lower thigh supporting base 58, thereby being able to be freely expanded and contracted and be freely mounted and dismounted.

In this regard, in FIG. 3, a reference numeral 108 denotes a screw member screwed into the side of the sleeve 58A to lock the rod 106A and provided with a handle, a reference numeral 110 denotes a sole putting member (on which the sole of the patient K is put) provided at the end of the lower thigh supporting base 58 in order to put the sole of the patient, and a reference numeral 111 denotes a band as fixing means for fixing the lower thigh K2 of the patient K. Then, the auxiliary table 106 is also provided with a band 106B as fixing means for fixing the lower thigh (K2), here, the lower leg K1 of the patient K.

The swing arm 52 can be expanded and contracted. Specifically, as shown in FIG. 1 and FIG. 3, the swing arm 52 is constructed of a first arm 52C on a base body side and a second arm 52D on a free end side. These first and second arms 52C, 52D are coupled to each other in such a way as to guide each other in the longitudinal direction. Then, as is evident from FIG. 1, similarly, a cover 55B for covering the swing arm 52 is also constructed of a first cover 55B1 and a second cover 55B2 that are coupled to each other in such a way as to guide each other in the longitudinal direction.

Then, bolt through holes 52D1 are formed in the second arm 52D and the second cover 55B2 at corresponding positions along the longitudinal direction at equal pitches and bolts 54 are passed through these bolt through holes (here, a reference numeral for bolt through holes formed in the second cover 55B2 is omitted). Then, screw holes 52C1 and 55B12 are formed in the first arm 52C and the second cover 55B1 in such a way as to correspond to the respective bolt through holes and the respective bolts 54 can be screwed in these screw holes 52C1, 55B12.

That is, the respective bolts 54 are loosened and hence released from the state where they are screwed in the respective screw holes 52C1 and 55B12. Then, the second arm 52D and the second cover 55B2 are moved with respect to the first arm 52C and the first cover 55B1 to expand or contract the whole of the swing arm 52 and the cover 55B to a desired length. Then, the respective bolts 54 are again screwed in the respective screw holes 55C1, 55B12.

In this regard, the swing arm 52 can be expanded or contacted not only by the above-mentioned manual operation but also by an automatic operation. Although not specifically shown, the automatic operation can be easily realized, for example, by providing arm expanding and contracting means including a ball screw mechanism shown in FIG. 4 and a driving mechanism such as a motor for operating the ball screw mechanism.

By the way, this physiotherapy unit 5 is provided with means for regulating a transmission force so as to prevent the apparatus from forcibly applying a force to the lower leg K1 at the time of reducing the lower leg K1 of the patient K. This means has an absolutely mechanical construction and the inventor calls this means a mechanical safety switch. The construction of this mechanical safety switch will be described.

In this regard, in the physiotherapy apparatus according to this one embodiment, the mechanical safety switches are provided at a driving part for twisting the lower leg K1 of the patient K (in the direction shown by arrow R) and a driving part for expanding and contracting the lower leg K1 (in the direction shown by arrow Y). The other driving parts for performing other operations, that is, the driving part for moving the lower leg K1 to the left and right (in the direction shown by arrow X), the driving part for moving the lower leg K1 up and down (in the direction shown by arrow Z), the driving part for bending the ankle K4 back and forth (in the direction shown by arrow Q), and the driving part for swinging the ankle K4 to the left and right (in the direction shown by arrow P) can be also provided with the mechanical safety switches, respectively, as required.

In FIG. 5 is shown a mechanical safety switch provided in a system for transmitting power from the first driving means 62 for twisting the lower leg K1 (in the direction shown by arrow R).

In FIG. 5, the first movable table 61 for moving the lower thigh supporting base 58 (refer to FIG. 1 and FIG. 3) around a horizontal axis (60) is shaped like a disk and is fixed to the output shaft 62A of the motor 62 of the first driving means for driving the first movable table 61. A protrusion 61A shaped like a circular column is formed at the rotational center of the first movable table 61 on the opposite side of the motor 62 and is rotatably fitted in a bearing 73C provided in the intermediary plate 73. With this, the intermediary plate 73 can be rotated freely with respect to the first movable table 61.

In the first movable table 61, a through hole 61B shaped like an ellipse in cross section, which is elongated in the radial direction, is formed at a position deviated from its rotational center. Meanwhile, in the intermediary plate 73, a through screw hole 73E is formed at a position corresponding to the through hole 61B and an adjustment screw 74A is screwed in this screw hole 73E. A steel ball 74B is arranged at the tip of the threaded portion of the adjustment screw 74A and is fitted in the screw hole 73E in such a way as to move freely.

Then, a coil spring 74C is provided in a contracted manner between the adjustment screw 74A and the steel ball 74B. With this, the steel ball 74B has a force applied thereto, thereby being pressed onto the through hole 61B by a specified pressing force. Here, the width of the through hole 61B is made smaller than the diameter of the steel ball 74B and hence the steel ball 74B is not put into the through hole 61B.

In the above-mentioned construction, in the case of twisting the lower leg K1 (in the direction shown by arrow R), the driving force from the motor 62 is transmitted to the lower thigh supporting base 58 via the first movable table 61, the steel ball 74B, the intermediary plate 73, and so on in succession. However, when a force is going to be forcibly applied to the lower leg K1 in the direction of twist, the steel ball 74B is released from the state of engagement with the through hole 61B against a force applied by the coil spring 74C, whereby the driving force is not transmitted to the lower leg K1. "The force applied forcibly" at this time is adjusted in advance by the quantity of screwing of the adjustment screw 74A.

Next, a mechanical safety switch provided in a system for transmitting power from the second driving means 68 (refer to FIG. 4) for expanding and contracting the lower leg K1 (in the direction shown by arrow Y) will be described on the basis of FIG. 6.

As shown in FIG. 6, an intermediate plate 96 is interposed between the second movable table 67 for moving the lower thigh supporting base 58 (refer to FIG. 1 and FIG. 3) in the nearly horizontal direction and the inner block 95 included by the second driving means 68. The intermediate plate 96 is fixed on the top surface of the inner block 95.

On the top surface of the intermediate plate 96, for example, two guide shafts 96A are arranged and fixed in such a way as to be parallel in the direction in which the inner block 95 is moved. Moving blocks 67A are fixed to the bottom surface of the second movable table 67 and are movably engaged with the guide shafts 96A. With this, the second movable table 67 can be freely reciprocated with respect to the inner block 95 and the intermediate plate 96 in the direction in which the inner block 95 is moved.

In the intermediate plate 96 is formed a through hole 96B shaped like an ellipse in cross section, which is elongated in the left and right direction (in the direction shown by arrow X). Meanwhile, in the second movable table 67, a through screw hole 67B is formed at a position corresponding to the through hole 96B and an adjustment screw 92A is screwed in the screw hole 67B.

Moreover, a steel ball 92B is arranged at the tip of the threaded portion of the adjustment screw 92A and is fitted in the screw hole 67B in such a way as to move freely. A coil spring 92C is provided in a contracted manner between the adjustment screw 92A and the steel ball 92B. With this, the steel ball 92B has a force applied thereto, thereby being pressed onto the through hole 96B by a specified pressing force. Here, the width of the through hole 96B is made smaller than the diameter of the steel ball 92B and hence the steel ball 92B is not put into the through hole 96B.

In the construction like this, in the case of expanding and contracting the lower leg K1 (in the direction shown by arrow Y), the driving force from the motor 97 (refer to FIG. 4 and the like) is transmitted to the lower thigh supporting base 58 via the inner block 95, the intermediate plate 96, the steel ball 92B, and the second movable table 67, and so on in succession. However, a force is going to be forcibly applied to the lower leg K1 in the direction of expansion and contraction, the steel ball 92B is released from the state of engagement with the through hole 96B against a force applied by the coil spring 92C, whereby the driving force is not transmitted to the lower leg K1. "The force applied forcibly" at this time is adjusted in advance by the quantity of screwing of the adjustment screw 92A.

(Control Section)

Next, a control section according to this one embodiment for controlling the physiotherapy unit 5 will be described. In FIG. 7 is shown this control section.

As shown in FIG. 7, the control section according to this one embodiment is provided with a control unit 113 for controlling the whole system, a force sensor 114 of a single component so constructed as to be able to detect a force applied to the lower leg K1 when the lower leg K1 is caused to perform various motions, a force displaying part 115 for displaying a force detected by the force sensor 114, and a portable operation box 117.

Then, a motor 120 included by the above-mentioned arm driving means and the respective motors 62, 97, 83, 102, 104 included by the first to fifth driving means are connected to the control unit 113 via drivers 118.

Then, the control unit 113 is constructed of an information processing part, which includes a CPU (central processing unit) and a memory such as a ROM and a RAM, and an auxiliary storage part. Then, the control unit 113 constructed in this manner is so constructed as to store applications based on a real time OS.

Moreover, various tasks such as a user task and a real-time task are combined with each other on the basis of the real-time OS in the control unit 113 so as to secure real time to thereby perform various processing for controlling the physiotherapy unit 5 by a control loop of, for example, 1 kHz. Then, the measurement value of a force measured by the force sensor 114 is supplied to the control unit 113 by data.

Next, the operation of the physiotherapy unit 5 constructed in the above-mentioned manner will be described. As shown in FIG. 1, at the time of giving the patient K physiotherapy for his lower leg K1, the lower half of the body of patient K is placed on the place base 50B of the support base 50 with the patient K put on his back and the upper half of the body is supported as appropriate by a table (not shown) or the like.

Then, the lower thigh K2 and the foot K3 of the patient K are put on the lower thigh supporting base 58 and the lower thigh K2 is fixed by a band 111.

Next, the operation box 117 is operated as appropriate according to the contents of physiotherapy to drive the swing arm 52, the first to third movable tables 61, 67, 64, or the coupling members 72A, 72B of the universal coupling 72. That is, as shown in FIG. 2, in the case of moving the lower leg K1 to the left and right (in the direction shown by arrow X), the swing arm 52 is swung in the X direction.

In the case of twisting the lower leg K1 (in the direction shown by arrow R), the first movable table 61 is rotated. In the case of moving the lower leg K1 up and down (in the direction shown by arrow Z), the third movable table 64 is driven up and down. Then, in the case of expanding and contracting the lower leg K1 back and forth (in the direction shown by arrow Y), the second movable table 67 is driven back and forth.

Furthermore, in the case of swing the ankle K4 to the left and right (in the direction shown by arrow P) the lower second coupling member 72B of the universal coupling 72 is rotated and driven in the same direction. Moreover, in the case of bending the ankle K4 back and forth (in the direction shown by arrow Q), the upper coupling member 72A of the universal coupling 72 is rotated and driven in the same direction.

In the above description, the physiotherapy apparatus is constructed in such a way that when the doctor and the like operate the operation box 117 referred to as a teaching pendant by the present inventor, the respective motors are operated to drive the swing arm 52 and the like to thereby move the lower leg K1 of the patient K in an appropriate direction.

However, meanwhile, it is necessary that the doctor and the like move the lower leg K1 by their forces to bring the lower leg K1 into a state most suitable for performing physiotherapy and causes the physiotherapy apparatus to recognize the state. In this case, even when the doctor and the like move the lower leg K1 of the patient K, a holding force by the driving system including the respective motors interferes with their action. Hence, the following construction is employed.

That is, the above-mentioned force sensor 114 is constructed in such a way as to be able to detect forces, which are applied in all directions of six axes (directions shown by arrows X, Y, Z, P, Q, and R), for example, by the doctor and the like, that is, forces from the outside. Then, the measurement values by this force sensor 114 are supplied as numerical data to the control unit 113 as a control section.

As shown in FIG. 1 and FIG. 3, the force sensor 114 is interposed between a seat portion 72A1 formed on the coupling member 72A included by the universal coupling 72 and a seat portion 110A formed on the back of a sole putting member 110 of the lower thigh supporting base 58.

Meanwhile, the operation box 117 shown in FIG. 7 is provided with a switch for switching the control of the physiotherapy apparatus between a case where the lower leg K1 is moved to a desired state by the actions of the respective motors and a case where the lower leg K1 is moved to a state most suitable for physiotherapy by the forces of the doctor. The control unit 113 performs different control on the physiotherapy apparatus according to the switching.

In the case of moving the lower leg K1 to a desired state by the actions of the respective motors, the physiotherapy apparatus is controlled in the manner described above, whereas in the case of switching so as to move the lower leg K1 to a state most suitable for physiotherapy by the forces of the doctor, the physiotherapy apparatus is controlled in the following manner.

(Power Assistance Control)

That is, when the doctor and the like are going to move the lower leg K1 in an arbitrary direction, a force in the direction is applied to the force sensor 114 and the force sensor 114 detects the direction of the force.

At this time, the control unit 113 drives a motor corresponding to the direction in a direction that reduces the force applied by the doctor and the like. Then, when the force detected by the force sensor 114 becomes zero, the control unit 113 stops the motor. Power assistance controlling drive like this will be specifically described below.

A power assistance driving system according to this one embodiment is a drive system of the type in which when a force applied to the foot K3 of the patient by the doctor and the like is detected by the force sensor 114, the positive feedback control of proportional control is performed to move the lower foot K3 of the patient to an arbitrary position.

Here, first, when the doctor and the like apply a force to the foot K3 of the patient, as required, to the foot K3 in a state where the foot K3 wears a boot, the force sensor 114 detects a vector sum of "a force being actually applied to the foot K3" which is actually being applied to the foot of the patient and "a force applied to the foot K3" which is a force that the doctor and the like apply to the foot K3 from the outside. In the power assistance control, it is absolutely necessary to detect a force that the doctor and the like apply to the foot K3 from the outside. However, it is difficult to detect "a force applied to the foot K3".

Then, in this one embodiment, a difference between a detection reference detected at the starting point of power assistance control and the measurement value of the force sensor 114, that is, a target assistance force is found by one force sensor 114 mounted on the physiotherapy apparatus.

That is, first, in order to start power assistance control, the doctor or the like presses a foot switch 121 shown in FIG. 7 (in FIG. 8A, at timing (1) TURN ON SEITCH (in the drawing, designated by a numeral in a circle)). At this time, the control unit 113 sets the value of the force sensor 114 at the timing of an instant when the doctor or the like presses the foot switch 121 as the origin of the target assistance force, that is, as a detection reference and measures a change in the measurement value of the force sensor 114 after the instant with respect to this origin of the target assistance force. Here, the measurement value by the force sensor 114 is shown by a solid line in FIG. 8A.

With this, the target assistance force can be detected and the effect of the self weight of the lower leg of the patient can be eliminated. Here, the point where the measurement value by the force sensor 114 becomes 0 (N), that is, a so-called true origin of the force sensor 114 is stored in the control unit 113.

Then, a force is manually applied to the foot K3 within a range necessary for physiotherapy by the doctor and the like. Then, the measurement value by the force sensor 114 varies by a large amount at the stage where the force is manually applied to the foot K3 by the doctor and the like (in FIG. 8A, at timing (2) APPLY FORCE TO FOOT (in the drawing, designated by a numeral in a circle)).

At this timing, the magnitude of the force applied by the doctor and the like, that is, "force applied to the foot K3" is set as a target assistance force. Then, the control unit 113 supplies the driver 118 with a signal so as to apply a driving force relating to this target assistance force to the foot K3, whereby the necessary motors of the motors 62, 83, 97, 102, 104, and 120 are driven in a direction in which the difference between the detection reference and this "force applied to the foot K3" is decreased. With this, a specified driving force is applied to the foot K3.

Moreover, as described above, the control unit 113 stores also the true origin of the force sensor 114. For this reason, from the true origin, the measurement value by the force sensor 114, and the magnitude of the "force applied to the foot K3" (in FIG. 8A, shown by a portion of "applied force") set in the above-mentioned manner, it is possible to achieve the essential object, that is, to detect "force being actually applied to the foot K3".

That is, "the force being actually applied to the foot K3" and "the force applied to the foot K3" can be detected by one force sensor 114 for measuring a force, whereby two objects can be achieved.

Then, in a state where the doctor and the like apply a force to the foot K3, an assistance force is applied to the foot K3 by the motors necessary for power assistance control drive of the motors 62, 83, 97, 102, 104, and 120 of the driving system.

In the case of increasing "the force being actually applied to the foot K3" as shown in a potion A in FIG. 8A in a state where the doctor and the like apply a force to the foot K3, the measurement value of the force sensor 114 (shown by solid line) increases. Here, the gradient of the measurement value of the force sensor 114 can be changed according to the conditions of the physiotherapy and setting by the doctor and the like. That is, by changing the speed of applying a force to a desired speed, a required speed can be obtained.

Then, as the measurement value by the force sensor 114 increases, the difference between the detection reference and the measurement value by the force sensor 114, that is, the target assistance force decreases as a whole. Then, as the target assistance force decreases, the driving force applied to the foot K3 also decreases.

When the target assistance force continues to decrease and hence the driving force applied to the foot K3 decreases, the measurement value by the force sensor 114 comes close to the detection reference. In accordance with this, the driving force applied to the foot K3 comes close to zero and hence the assistance operation proceeds in a direction to stop.

Then, as shown by a C portion in FIG. 8A, when an increase in "the force being actually applied to the foot K3" balances with "the force applied to foot K3", that is, the measurement value of the force sensor 114 reaches an assistance origin (detection reference), the target assistance force becomes 0 (N). With this, the driving force applied to the foot K3 is brought to 0 to stop the assistance operation. Here, even when the assistance operation is stopped, the above-mentioned assistance operation can be continued again by stepping on the foot switch 121 again.

Then, in this one embodiment, a specification is employed in which the doctor or the like takes his foot off the foot switch 121 to release the driving force to stop the assistance operation. In other words, this embodiment is constructed in such a way that when an operator such as the doctor perceives abnormality, the operator can stop driving the apparatus immediately.

The power assistance control drive according to this one embodiment is performed in the manner described above. While the force applied to the foot K3 by the doctor or the like is applied only in one direction and hence the driving force in the assistance operation is applied only in one direction in the above description, the direction of the driving force in the assistance operation can be reversed. An example of power assistance control in this case is shown in FIG. 8B.

As shown in FIG. 8B, in the case where the direction of assistance in the power assistance control is reversed, as is the case in FIG. 8A, when the doctor or the like applies a force to the foot K3 in one direction, the power assistance control is effected. Then, according to need of physiotherapy, when the doctor or the like reverses the direction in which the force is manually applied to the foot K3, as is the case where the doctor or the like takes his hand off as described above, the measurement value of the force sensor 114 once agrees with "the force being actually applied to the foot K3".

Then, also in this case, the assistance operation is effected in a direction that decreases the target assistance force, which is the difference between the assistance origin of the detection reference and the measurement value of the force sensor 114.

At this time, as shown in FIG. 8B, after the startup of the assistance operation, the direction of the driving force by the assistance control is reversed in a direction opposite to the direction of the force at timing when the doctor or the like applies a force to the foot K3 (at timing (2) APPLY FORCE TO FOOT (in FIG. 8, designated by a numeral in a circle, ditto for the following)). That is, the direction of the target assistance force is reversed in the midstream of the assistance operation.

For this reason, the assistance operation proceeds in a direction to return to the assistance origin (detection reference). Then, when the target assistance force becomes zero, the assistance operation is stopped.

Moreover, the doctor or the like presses the foot switch 121 to turn on the power assistance control (in FIG. 8B, at timing (1) TURN ON SWITCH). When the doctor or the like takes off his hand to release a force applied to the foot K3 in this state where the power assistance control is on (in FIG. 8B, at timing (3) RELEASE FORCE), at this timing, an increase in "the force being actually applied to the foot K3" is regarded as the difference between the detection reference and the measurement value of the force sensor 114, that is, the target assistance force. For this reason, the power assistance control will be returned to a state where the foot switch 121 is pressed and hence is operated in a safe state.

By the power assistance control performed in the manner described above, the lower leg K1 is moved only by the amount moved by the doctor or the like and when the doctor or the like stops applying a force to the lower leg K1, the lower leg K1 can be kept in the state of stop by the holding force of the driving system (motor and the like).

As described above, the algorithm of this power assistance driving system can enhance safety for the patient and hence can be applied also to other medical use and architectural use.

Moreover, in the physiotherapy apparatus according to this one embodiment, in addition to the above-mentioned power assistance driving system, two driving systems of a JOG driving system and a spline driving system are provided as a fundamental driving system.

(Spline Interpolation Driving System)

Furthermore, a physiotherapy apparatus according to this one embodiment can employ also a spline interpolation driving system. In the spline interpolation driving system, the physiotherapy apparatus is driven along a trajectory formed by interpolating a train of control points sent from a higher level system by a three-dimensional spline.

According to the spline interpolation driving system, it is possible to realize a smooth trajectory in a state where the amount of communication is decreased. While the spline interpolation driving system is driven by speed control, this algorithm is so constructed as to make a correction always at the time of updating a control point and hence has an advantage of eliminating the accumulation of errors.

(Verification Test on Trajectory Accuracy)

The present inventor gave the physiotherapy apparatus according to this embodiment five control points, which were thought to be given by a command from a higher level system, and drove the physiotherapy apparatus in such a way that the physiotherapy apparatus passed a total of 251 points obtained by dividing each section between the five control points into 50 portions by the use of spline interpolation.

Then, the inventor measured the driving of the physiotherapy apparatus by the use of a three-dimensional position measuring device and compared the measurement values with coordinates obtained by the spline interpolation computation to determine the deviations of the measurement values from the coordinates. This result is shown in FIG. 9. A driving speed was set at 10 mm/sec, which is the maximum design speed of the spline driving.

From FIG. 9A, it is found that the average value and the maximum value of the deviations in a translational motion are 0.51 (mm) and 1.05 (mm). Then, from FIG. 9B, it is found that the average value of the deviations in a rotational motion is 2.16 (mrad). According to the inventor's findings and study, these deviations are thought to be produced in proportion to the driving speed.

Hence, it was verified that the position control accuracy of a robot driven at a low speed was sufficient and hence could improve the performance of the physiotherapy apparatus.

(JOG Driving System)

JOG driving system performs a step operation, for example, for each 10 mm for a translational axis and for 6° for a rotational axis according to an instruction from the operation box 117 referred to as a teaching pendant. Then, in the case of using a higher level system, an arbitrary amount of driving can be specified.

(Communication With Higher Level System)

Next, communication with a higher level system in a physiotherapy apparatus according to one embodiment of this invention will be described.

That is, the present inventor proposed a communication protocol for general purpose use by which a higher level system could communicate with a physiotherapy apparatus and a communication API (Application Program Interface) for facilitating integration into a higher level system. Here, this communication protocol is adaptable to multiple clients and can control a physiotherapy apparatus and can receive the status of a physiotherapy apparatus through an Ethernet (registered trademark).

Moreover, a physiotherapy navigation system for a bone fracture between trochanters of a femur can be also employed as one of the higher level systems. By employing this navigation system, the conditions of the affected part of the patient can be grasped in real time and hence the affected part can be reduced by computing a reduction trajectory and by providing the physiotherapy unit 5 with an instruction. With this, it is possible to enhance reduction accuracy and to decrease the amount of exposure dose of the doctor or the like in performing physiotherapy by a large amount.

Up to this point, one embodiment of this invention has been specifically described. However, it is not intended to limit this invention to the above-mentioned embodiment, but it should be understood that other various modifications based on the technical principles of this invention can be made.

For example, the numerical values in the above-mentioned one embodiment are only examples and numerical values different from these can be used as required.

For example, by providing arm driving means 120 for driving the swing arm 52, the swing arm 52 can be automatically swung without depending on a manual force.

Moreover, for example, by enabling the swing arm 52 to expand and contract, the swing arm 52 can be expanded and contracted as appropriate even if the patient K has any physical constitution, for example, a small constitution, a large constitution, an adult, or a child.

Furthermore, for example, by providing arm expanding/contracting means for expanding and contracting the swing arm 52, the swing arm 52 can be automatically expanded and contracted and hence a manual force can be decreased to a minimum necessary amount.

Still furthermore, for example, the swing arm 52 moves the lower leg K1 to the left and right, and the first movable table 61 twists the lower leg K1, and the second movable table 67 expands and contracts the lower leg K1, and the third movable table 64 moves the lower leg K1 up and down. This construction is suitable for causing the doctor or the like to perform physiotherapy freely.

Still furthermore, for example, the swing arm 52, the first movable table 61, the second movable table 67, the third movable table 64, and the lower thigh supporting base 58 can be mounted stepwise in a specified order, for example, in the order described in this one embodiment. In this case, the construction can be simplified as compared with the case of mounting the respective parts independently and separately.

Still furthermore, for example, the lower thigh supporting base 58 is provided with fixing means (such as the band 111) for fixing the lower thigh K2 of the patient K. As a result, the force can be effectively transmitted from the lower thigh supporting base 58 to the leg of the patient K.

Still furthermore, there are provided the coupling members 72A, 72B and hence the lower thigh supporting base 58 can be moved freely around the nearly horizontal axis or the nearly vertical axis. As a result, the ankle K4 can be bent back and forth and swung to the left and right.

The respective operations that the physiotherapy apparatus causes the lower leg K1 and the ankle K4 to perform can be performed independently, but two or more operations can be also performed at the same time. For example, by driving the swing arm 52 and the coupling members 72A, 72B at the same time, the lower leg K1 can be moved to the left and right and at the same time the ankle K4 can be bent back and forth.

Still furthermore, the lower thigh supporting base 58 is provided with the auxiliary member (auxiliary table 106) capable of expanding and contracting freely in the longitudinal direction of the lower thigh K2 and being freely mounted and dismounted. As a result, by mounting the auxiliary member on the lower thigh supporting base 58 and supporting the whole of lower thigh K2 in a state where the lower thigh K2 is expanded, the load applied to the patient K can be decreased. Moreover, when an X-ray radiograph is taken, the auxiliary member can be decreased in size or removed to thereby prevent the auxiliary member from coming out in the X-ray radiograph.

Still furthermore, the lower thigh supporting base 58 is provided with the sole putting member 110 to which the sole of patient put. As a result, at the time of expanding and contracting the lower leg K1 back and forth or at the time of bending the ankle K4 back and forth or swinging the ankle K4 to the left and right, the force can be applied to the whole sole of the patient K. With this, giving the patient K an unnecessary pain can be prevented.

Then, in the above-mentioned one embodiment has been shown a case where the driving means (arm driving means) for swinging the swing arm 52 of the physiotherapy unit 5 is provided, but this driving means does not always need to be provided. In the case where the driving means is not provided, the swing arm 52 is manually swung to and positioned at a desired position.

Then, this invention can be applicable not only to the physiotherapy apparatus but also to all apparatuses such as earthmoving apparatuses used for civil engineering works that detect forces from outside and assist a force to be applied.

Furthermore, a device having switches protruded outward as shown in FIG. 7 is used as the operation box 117 in the above-mentioned one embodiment. However, this operation box 117 can also employ a construction capable of displaying various kinds of switches as shown in FIG. 7 on a touch panel and performing the same operations performed by using buttons. Even in this case, it is desirable that an emergency stop button for stopping driving the apparatus in the event of emergency is constructed of a button protruded from the touch panel.

The invention claimed is:

1. A power assistance controlling apparatus comprising:
   force detecting means constructed so as to detect a force applied to an object and having one detection point, and detecting a force manually applied to the object from outside and a force applied to the object separately of the manually applied force and varies when the force is manually applied to the object from outside;
   driving means for applying a force to the object;
   switching means for controlling turning on/off the driving means; and
   control means for controlling the driving means and constructed so as to communicate data with the force detecting means,
   wherein the force detecting means measures a force including the resultant force of the force manually applied to the object from outside and the force actually applied to the object separately of the manually applied force and varies when the force is manually applied to the object from outside with reference to a detection reference force, the detection reference force being a force measured by the force detecting means in response to the switching means turning on the driving means, and
   wherein the driving means applies an assistance force to the object in such a way as to decrease a difference between the measured force including the resultant force measured by the force detecting means and the detection reference force.

2. The power assistance controlling apparatus according to claim 1, wherein a force applied to the object by the driving means is applied until a difference between the measured force including the resultant force and the detection reference force comes nearly to zero.

3. The power assistance controlling apparatus according to claim 1 or 2, wherein the force detecting means is a six-axial force sensor capable of detecting forces applied in translational three axial directions and in rotational three axial directions.

4. A power assistance controlling method, comprising:
   detecting a force including a resultant force of a force manually applied to an object from outside and a force applied to the object separately of the manually applied force and varies when the force is manually applied to the object from outside by a force detecting means having one detection point and constructed so as to detect the force applied to an object and detecting the force manually applied to the object from outside and the force applied to the object separately of the manually applied force and varies when the force is manually applied to the object from outside;
   measuring a detection reference force, the detection reference force being a force measured by the force detecting means in response to a switching means for controlling turning on/off the driving means turning on the driving means which applies the force to the object;

applying manually the force to the object from outside;

measuring the force including the resultant force by the force detecting means with reference to the detection reference force; and applying an assistance forced to the object by the driving means in such a way as to decrease a difference between the force including the resultant force measured when the force is manually applied to the object from outside and the detection reference force.

5. The power assistance controlling method according to claim 4, wherein a force is applied to the object by the driving means until a difference between the force including the resultant force measured when the force is manually applied to the object from outside and the detection reference comes nearly to zero.

6. The power assistance controlling method according to claim 4 or 5, wherein the force detecting means is a six-axial force sensor, and further comprising:

detecting forces applied in translational three axial directions and in rotational three axial directions with the force detecting means.

7. A physiotherapy apparatus comprising:

a power assistance controlling mechanism that includes:

force detecting means constructed so as to detect a force applied to an object and having one detection point, and detecting a force manually applied to the object from outside and a force applied to the object separately of the manually applied force and varies when the force is manually applied to the object from outside;

driving means for applying a force to the object;

switching means for controlling turning on/off the driving means; and control means for controlling the driving means and constructed so as to communicate data with the force detecting means, and is constructed in such a way that a force including the resultant force of the force manually applied to the object from outside and the force applied to the object separately of the manually applied force and varies when the force is manually applied to the object from outside is measured by the force detecting means with reference to a detection reference force, the detection reference force being a force measured by the force detecting means in response to the switching means turning on the driving means and that the driving means applies an assistance force to the object in such a way as to decrease a difference between the measured force including the resultant force and the detection reference force.

* * * * *